(12) United States Patent
Kerr et al.

(10) Patent No.: US 10,888,548 B2
(45) Date of Patent: *Jan. 12, 2021

(54) ANTI-DANDRUFF COMPOSITIONS COMPRISING A SPIROFURANONE LACTAM TETRAMIC ACID DERIVATIVE

(71) Applicant: Croda International PLC, Yorkshire (GB)

(72) Inventors: Russell Greig Kerr, Charlottetown (CA); David Patrick Overy, Carleton Place (CA); Fabrice Berrué, Halifax (CA)

(73) Assignee: Croda International Plc (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/580,017

(22) PCT Filed: Jun. 8, 2016

(86) PCT No.: PCT/GB2016/051681
§ 371 (c)(1),
(2) Date: Dec. 6, 2017

(87) PCT Pub. No.: WO2016/198850
PCT Pub. Date: Dec. 15, 2016

(65) Prior Publication Data
US 2018/0177762 A1 Jun. 28, 2018

(30) Foreign Application Priority Data

Jun. 8, 2015 (GB) .................................. 1509849.4

(51) Int. Cl.
| | | |
|---|---|---|
| A61K 31/407 | (2006.01) | |
| A61K 31/336 | (2006.01) | |
| A61Q 5/00 | (2006.01) | |
| A61K 31/4025 | (2006.01) | |
| A61K 8/49 | (2006.01) | |
| C12P 17/16 | (2006.01) | |
| C12P 17/18 | (2006.01) | |
| C12R 1/645 | (2006.01) | |

(52) U.S. Cl.
CPC .......... *A61K 31/407* (2013.01); *A61K 8/4973* (2013.01); *A61K 31/336* (2013.01); *A61K 31/4025* (2013.01); *A61Q 5/006* (2013.01); *C12P 17/162* (2013.01); *C12P 17/182* (2013.01); *C12R 1/645* (2013.01)

(58) Field of Classification Search
CPC .............. A61K 31/4071; A61K 8/4973; A61K 31/336; A61K 31/4025; A61Q 5/006; C12P 17/162; C12P 17/182
USPC ........................................................ 514/409
See application file for complete search history.

(56) References Cited

U.S. PATENT DOCUMENTS

| | | |
|---|---|---|
| 2010/0184853 A1 | 7/2010 | Hernandez et al. |
| 2019/0110973 A1* | 4/2019 | Kerr .................. A61K 8/49 |

FOREIGN PATENT DOCUMENTS

| | | |
|---|---|---|
| EP | 0546474 A1 | 6/1993 |
| JP | 01277492 A | 11/1989 |
| KR | 20110087395 A | 8/2011 |
| WO | 2007096654 A2 | 8/2007 |
| WO | 2008152127 A1 | 12/2008 |
| WO | 2013050241 A1 | 4/2013 |

OTHER PUBLICATIONS

Hsiao et al., "Pycnidione, a Fungus-derived Agent, Induces Cell Cycle Arrest and Apoptosis in A549 Human Lung Cancer Cells", Chemico-Biological Interactions 197, 2012, pp. 23-30.
International Search Report and Written Opinion for International Application No. PCT/GB2016/051681, dated Aug. 10, 2016, 10 Pages.
Ishikawa et al., "Pseurotin a and its Analogues as Inhibitors of Immunoglobuline E Production", Bioorganic & Medicinal Chemistry Letters, vol. 19, 2009, pp. 1457-1460.
Kang et al., "Culture Condition-dependent Metabolite Profiling of Aspergillus fumigatus with Antifungal Activity", Fungal Biology, 117, 2013, pp. 211-219.
Mo et al., "Naturally Occurring Tetramic Acid Products: Isolation, Structure Elucidation and Biological Activity", RSC Adv., vol. 4, 2014, pp. 50566-50593.
Overy et al., "Sea Foam as a Source of Fungal Inoculum for the Isolation of Biologically Active Natural Products", Mycology:International Journal on Fungal Biology, vol. 5, No. 3, Sep. 19, 2014, pp. 130-144.
Wanner et al., "Epolones Induced Erythropoietin Expression via Hypoxia-inducible Factor-1 α Activation", Blood, Aug. 15, 2000, vol. 96, No. 4. pp. 1158-1565.
Boerema, G., "Contributions Towards a Monograph of Phoma (Coelomycetes)—II Section Peyronellaea", Persoonia—Molecular Phylogeny and Evolution of Fungi, Jan. 1, 1993 pp. 197-221.
Database Registry [Online] Chemical Abstracts Service, Columbus, Ohio, US, Mar. 26, 2010, XP002760624—1 page.

(Continued)

*Primary Examiner* — Yevgeny Valenrod
(74) *Attorney, Agent, or Firm* — RatnerPrestia

(57) ABSTRACT

Anti-Dandruff Agents A novel anti-dandruff composition comprising spirofuranone-lactam tetramic acid or derivatives thereof, and optionally at least one biologically derivable meroterpene. The spirofuranone-lactam tetramic acid is preferably a bio-active heterospirocyclic secondary metabolite of *Aspergillus*, such as pseurotin A. The biologically derivable meroterpene may be selected from fumagillin, fumagillin derivative, chlovalicin, or ovalicin. Use of said agents as anti-dandruff actives in anti-dandruff compositions, particularly shampoos and conditioners is also provided. The active is particularly effective against *Malassezia* yeasts and *Malassezia furfur* which may cause dandruff. A method of obtaining the anti-dandruff actives from culturing of *Peyronellaea* sp. strain RKDO347 is also described.

17 Claims, No Drawings

(56) References Cited

OTHER PUBLICATIONS

International Search Report and Written Opinion for International Application No. PCT/GB2016/051680, dated Sep. 23, 2016—16 Pages.
Non Final Office Action for U.S. Appl. No. 15/580,019, dated Dec. 12, 2019, 15 pages.
Final Office Action for U.S. Appl. No. 15/580,019, dated Apr. 3, 2020, 5 pages.
Notice of Allowance for U.S. Appl. No. 15/580,019, dated Jul. 13, 2020, 12 pages.

* cited by examiner

ANTI-DANDRUFF COMPOSITIONS COMPRISING A SPIROFURANONE LACTAM TETRAMIC ACID DERIVATIVE

CROSS REFERENCE TO RELATED APPLICATIONS

This application is the National Stage filing of International Appln. No. PCT/GB2016/051681, filed Jun. 8, 2016, and claims priority of GB Application No. 1509849.4, filed Jun. 8, 2015, the entirety of which applications is incorporated herein by reference for all purposes.

The invention relates generally to the use of a combination of biologically active compounds including a biologically derivable meroterpene with a spirofuranone-lactam tetramic acid or derivatives thereof, and the use of this combination as an anti-dandruff agent.

Anti-dandruff compositions, particularly shampoos, are well known and have been commercially available for many years. Many anti-dandruff actives have been used commercially such as ketoconazole, zinc pyrithione, piroctone olamine, octopirox, salicylic acid, selenium sulphide, coal tar, and azelaic acid. These actives generally function as anti-microbial/fungal agents, being effective against certain species and strains of fungi and/or bacteria. For example, the yeast-like fungus *Malassezia* lives on the scalp of most adults, but for some people it irritates the scalp and can cause more skin cells to grow. Although *Malassezia* yeasts are a part of the normal microflora, under certain conditions they can cause superficial skin infection. These extra skin cells die and fall off, making them appear white and flaky in hair and on clothes. Thus, materials which are active against *Malassezia*, in particular the species *Malassezia furfur*, can reduce the severity of dandruff.

These topic antifungal preparations are often combined with a cortisonic drug to control the inflammation and alleviate the pain and itching. However, the use of these molecules may not produce satisfactory results, and in some cases these compounds exhibit an intrinsic and undesired cytotoxicity.

Based on these findings, there is a need for compounds which demonstrate anti-fungal activity against *Malassezia* yeasts. There is a continual requirement for improved anti-dandruff actives and end-use products containing such actives. There is a need for anti-dandruff actives that have improved, including broad spectrum, activity against fungi and/or bacteria, or that function other than by antimicrobial effects; that do not have the environmental concerns of some existing actives, and/or in use are non-irritant to the skin.

There is also a need for an anti-dandruff effect to be obtained from the use of a wide range of hair care products such as a shampoo, conditioner, 2-in-1 shampoo/conditioner, leave-on hair tonic, spray, liquid rinse, gel or mousse etc. Ideally, an anti-dandruff active should be capable of being effective in a wide range of hair care products.

The present invention also seeks to provide compounds in a hair care formulation, where the compound may provide comparable or improved anti-dandruff properties compared to existing anti-dandruff agents.

The present invention also seeks to provide the use of compounds as anti-dandruff agents, and formulations comprising said compounds for use in reducing dandruff on human skin.

According to a first aspect of the present invention there is provided an anti-dandruff composition comprising an effective amount of at least one spirofuranone-lactam tetramic acid or derivatives thereof, and optionally at least one biologically derivable meroterpene.

According to a second aspect of the present invention there is provided a method of forming an anti-dandruff composition which comprises mixing together:
  (i) spirofuranone-lactam tetramic acid or derivatives thereof;
  (ii) at least one surfactant;
  (iii) water; and
  (iv) optionally at least one biologically derivable meroterpene.

According to a third aspect of the present invention there is provided the use of spirofuranone-lactam tetramic acid or derivatives thereof, and optionally at least one biologically derivable meroterpene, as active ingredients in an anti-dandruff composition.

According to a fourth aspect of the present invention there is provided an anti-dandruff shampoo or conditioner comprising:
  spirofuranone-lactam tetramic acid or derivatives thereof;
  a surfactant;
  optionally at least one biologically derivable meroterpene; and
  optionally one or more of a betaine, a non-ionic surfactant, an amphoteric surfactant, and a cationic surfactant.

According to a fifth aspect of the present invention there is provided a method of providing anti-dandruff efficacy which comprises the steps of:
  (i) wetting the hair with water;
  (ii) applying an effective amount of an anti-dandruff composition comprising spirofuranone-lactam tetramic acid or derivatives thereof, and optionally at least one biologically derivable meroterpene, to the hair;
  (iii) rinsing the anti-dandruff composition from the hair using water; and
  (iv) optionally repeating steps (ii) and (iii).

According to a sixth aspect of the present invention there is provided a method for killing or retarding the growth of *Malassezia* spp., the method comprising the step of contacting the *Malassezia* spp. with a composition comprising spirofuranone-lactam tetramic acid and optionally at least one biologically derivable meroterpene, effective to kill or retard the growth of *Malassezia* spp.

According to a seventh aspect of the present invention there is provided the use of a combination of at least one biologically derivable meroterpene and a spirofuranone-lactam tetramic acid or derivatives thereof, to provide a synergistic anti-dandruff effect.

According to an eighth aspect of the present invention there is provided a method of obtaining anti-dandruff actives according to the first aspect comprising the steps of: culturing *Peyronellaea* sp. in a medium under conditions which promote the metabolic synthesis of the anti-dandruff actives according to the first aspect from the *Peyronellaea* sp.; and purifying the synthesised active from the cultured medium.

According to a ninth aspect of the present invention there is provided an organism consisting of *Peyronellaea* sp., strain RKDO347, Canadian Collection of Fungal Cultures accession number DAOMC 250152.

We have surprisingly found novel anti-dandruff agents which either alone or in combination, namely at least one biologically derivable meroterpene with a spirofuranone-lactam tetramic acid or derivatives thereof, provides for a particularly advantageous anti-dandruff composition that overcomes and/or significantly reduces at least one of the aforementioned problems.

It has been found that the spirofuranone-lactam tetramic acid alone, or the specified combination provides for good anti-dandruff properties, and also has good cytotoxicity, formulability, and is active at lower pH.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

The term 'anti-dandruff composition' refers to the provision of effects for preventing and/or treating scalp dandruff. This includes preventing and/or reducing excessive dandruff formation, and/or visually unappealing excessively formed dandruff.

It will be understood that, when describing the number of carbon atoms in a substituent group (e.g. '$C_1$ to $C_6$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

The term 'anti-dandruff actives' refers collectively to the spirofuranone-lactam tetramic acid alone or in combination with at least one biologically derivable meroterpene. Any such references will be understood to include any combination of the any of the individual meroterpene actives with spirofuranone-lactam tetramic acid.

The term 'meroterpene' will be understood to include chemical compounds having a partial terpenoid structure.

The term 'biologically derivable' will be understood to include compounds which are producible and extractable from biological material, including microorganisms and in particular unicellular microorganisms. Preferably, the microorganisms may be selected from yeasts, fungi, or bacteria. Whilst the compounds should be derivable from biological microorganisims, this is not intended to limit to meroterpenes only derivable from this source, or to limit the scope of the claims to meroterpenes which have been derived as such. It will be appreciated that a number of routes are available to production of suitable meroterpenes, and that the intended limitation is only to those which may be biologically derived. The meroterpenes of the present invention may be obtained from any source and by any method known to the person skilled in the art.

The biologically derivable meroterpene may be selected from at least one fumagillin, fumagillin derivative, chlovalicin, or ovalicin, or may be any combination thereof. Preferably, the biologically derivable meroterpene is fumagillin or fumagillin derivative.

The biologically derivable meroterpene may be selected from those having a general structure of formula (I);

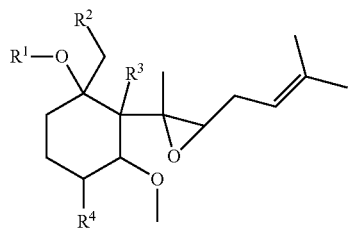

(I)

wherein:
$R^1$ independently represents hydrogen and $R^2$ independently represents chlorine, or $R^1$ and $R^2$ together represent a single bond to form an epoxide ring;
$R^3$ independently represents hydrogen or hydroxyl;
$R^4$ independently represents a hydroxyl, oxygen, or —OC(O)—[CH=CH—]$_n$R$^5$ group wherein R$^5$ represents a $C_2$-$C_4$ alcohol or diol, a $C_2$-$C_4$ optionally substituted epoxide, or a carboxyl group; and
n represents an integer in the range from 1 to 6.

The term 'hydroxyl' as used herein, unless otherwise stated, refers to a hydroxyl radical comprising one oxygen and one hydrogen atom having the structure —O—H, and which is bonded to an adjacent radical via the oxygen.

It will be understood when $R^4$ is oxygen, the oxygen forms a double bond to the ring carbon to which it is attached, and therefore forms a carbonyl group (—C=O).

The term '$C_2$-$C_4$ alcohol or diol' as used herein, unless otherwise defined, refers to saturated alcohol or diol radicals being straight chain and containing 2 to 4 carbon atoms. Preferably, containing 2 to 3 carbon atoms. More preferably, 3 carbon atoms.

It will be understood that the alcohol or diol is bonded to an adjacent radical via one of the carbon atoms in the said alcohol or diol.

Examples of $C_2$-$C_4$ alcohol or diol radicals may be independently selected from ethanol, 1-propanol, n-butanol, 2-butanol, isopropyl alcohol, isobutanol, tert-butyl alcohol, ethane-1,2-diol (ethylene glycol), 1,2-butanediol, 1,3-butanediol, 1,4-butanediol, 2,3-butanediol, propane-1,2-diol (propylene glycol), or 1,3-propanediol. Preferably, said radical is a $C_2$-$C_4$ diol. More preferably, the $C_2$-$C_4$ alcohol or diol radicals may be selected from isopropyl alcohol, propane-1,2-diol (propylene glycol), or 1,3-propanediol. Most preferably, the $C_2$-$C_4$ alcohol or diol radicals is propane-1,2-diol (propylene glycol).

The $C_2$-$C_4$ epoxide may be a cyclic three membered ether ring, and bonded to an adjacent radical via one of the carbon atoms in the said epoxide. The $C_2$-$C_4$ epoxide may optionally be substituted with an alkyl, preferably a $C_1$-$C_6$ alkyl.

The term '$C_1$-$C_6$ alkyl' as used herein, unless otherwise defined, refers to saturated hydrocarbon radicals being straight chain, branched, or cyclic moieties, containing 1 to 6 carbon atoms. Preferably, the alkyl groups each contain 1 to 3 carbon atoms. More preferably, 1 carbon atom.

Examples of alkyl radicals may be independently selected from methyl, ethyl, n-propyl, isopropyl, n-butyl, isobutyl, sec-butyl, tert-butyl, 2 methyl-butyl, pentyl, hexyl, cyclohexyl, or the like. Preferably, the alkyl radical is selected from methyl, ethyl, n-propyl, or isopropyl. More preferably, methyl or ethyl. Most preferably, it is methyl.

In a preferred embodiment the optionally substituted $C_2$-$C_4$ epoxide is propylene oxide or 1,2-epoxybutane. Preferably, propylene oxide.

The term 'carboxyl' as used herein refers to a carboxyl radial having a formula —C(O)OH.

It will be understood that the value 'n' is an integer and represents the number of repeat ethylene units present. Preferably, n is an integer of from 1 to 4. More preferably, n is an integer of from 1 to 3. Most preferably, n is an integer of 1. In an alternative embodiment, n is preferably 1 or 4.

A preferred biologically derivable meroterpene is one in which;
$R^1$ may be hydrogen and $R^2$ may be selected from chlorine, or $R^1$ and $R^2$ together represent a single bond to form an epoxide ring;
$R^3$ may be hydroxyl;
$R^4$ may be oxygen.

In an alternative embodiment a preferred biologically derivable meroterpene is one in which;

$R^1$ and $R^2$ together represent a single bond to form an epoxide ring;

$R^3$ may be hydroxyl;

$R^4$ may be hydroxyl or —OC(O)—[CH=CH—]$_n$R$^5$ group wherein $R^5$ may represent propane-1,2-diol, propylene oxide, or carboxyl; and where n may be 1 or 4.

In a particularly preferred embodiment a preferred biologically derivable meroterpene is one in which;

$R^1$ and $R^2$ together represent a single bond to form an epoxide ring;

$R^3$ may be hydroxyl;

$R^4$ may be hydroxyl or —OC(O)—[CH=CH—]$_n$R$^5$ group wherein $R^5$ represents propane-1,2-diol or propylene oxide when n is 1, or $R^5$ represents carboxyl or propylene oxide when n is 4.

The anti-dandruff composition also comprises at least one spirofuranone-lactam tetramic acid. In particular, the spirofuranone-lactam tetramic acid may be a bio-active heterospirocyclic secondary metabolite of *Aspergillus*.

These bio-active heterospirocyclics may be obtainable as, for example, secondary metabolites of, for example, *Aspergillus*. In particular, bio-active heterospirocyclics selected from pseurotin and variants thereof may be particularly preferred.

Suitable bio-active heterospirocyclics may be selected from the group comprising pseurotin A, pseurotin A$_1$, pseurotin A$_2$, pseurotin B, pseurotin C, pseurotin E, pseurotin D, pseurotin F$_1$, pseurotin F$_2$, asaspirenen, and synerazol. Preferably, the bio-active heterospirocyclics may be selected from pseurotin A, pseurotin A$_1$, and pseurotin A$_2$. Most preferably, the bio-active heterospirocyclic is pseurotin A.

It is observed that a synergistic anti-dandruff effect may be observed when the biologically derivable meroterpene and spirofuranone-lactam tetramic acid are used in combination as anti-dandruff actives.

The actives of the present invention may be produced and extracted from a biological organism by fermentation. The organism employed in the fermentation is desirably yeast. It has been found that certain strains of *Peyronellaea* sp. are especially useful in producing the novel anti-dandruff actives, and this strain have been made the subject of a deposit, under the Budapest Treaty, at the Canadian Collection of Fungal Cultures, Agriculture and Agri-Food Canada, Rm. 1015, K. W. Neatby Building, 930 Carling Avenue, Ottawa, Ontario, K1A 006, Canada:

| Species | Strain | Accession No. | Date of Deposit |
|---|---|---|---|
| *Peyronellaea* sp. | RKDO347 | DAOMC 250152 | 30 Mar. 2015 |

*Peyronellaea* sp. is especially preferred in providing the anti-dandruff actives of the present invention.

The biologically derivable meroterpene, and preferably chlovalicin, ovalicin, fumagillin, or the funagillin derivatives, may be obtained by isolation from microorganisms as known in the art. Alternatively, they may be obtained with known organic synthetic procedures. The desired compounds can be extracted and purified from the culture liquid or the fungal biomass by any means ordinarily used for generally collecting microbial metabolites. Examples include chromatography with adsorbent such as various ion exchange resins, non-ionic adsorbing resins, gel filtration chromatography, activated charcoal, alumina and silica gel, or a separation method by using high performance liquid chromatography, or crystallisation, concentration under reduced pressure, or lyophilisation, which means can be used alone or in appropriate combination thereof, or repeatedly.

The cultures of *Peyronellaea* sp., can be obtained from natural sources or from culture collections such as Canadian Collection of Fungal Cultures (CCFC; Ottawa, Canada). Isolates can be cultured by methods known in the art of mycology.

As a means of producing the compounds of the present invention, the producing organism can be grown on any suitable synthetic mediums or natural mediums so long as they appropriately contain carbon sources, nitrogen sources, and inorganic salts. If necessary, mediums may be suitably supplemented with vitamins and other nutrient substances. Examples of general carbon sources include (but are not limited to), sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates. As well micro-nutrients in the form of inorganic salts can be used, for example, calcium carbonate, sodium chloride, potassium chloride, magnesium sulphate, copper sulphate, manganese chloride, zinc sulphate, cobalt chloride, and various phosphates.

The organism can be grown in an appropriate cultivation temperature within a range that allows growth of a microorganism and effective production of the compounds of the present invention. Preferred cultivation temperature is from 10° C. to 32° C., and more preferably from 20° C. to 25° C. pH at the beginning of the cultivation is preferably from about 6 to 8, and cultivation period of time is generally about one day to a few weeks.

The cultivation may be terminated when a produced amount of the compound of the present invention reaches to an amount suitable for collection, preferably reaches to the maximum amount. As a cultivation method, any method can be suitably employed so far that the method is an ordinarily used, such as solid layer cultivation and normal stirring cultivation.

For example, isolates can be plated onto nutrient-containing (e.g., YM (Yeast extract Malt extract)) agar, and incubated for several days at room temperature until observable colonies appear. Individual colonies on the agar can be assayed for production of meroterpenes.

Those colonies producing the desired molecules can be used to inoculate a broth culture (e.g. a YM broth culture), which can be cultured under suitable conditions (e.g. at room temperature with shaking for several days) to yield a seed inoculum. The seed inoculum can be used to initiate larger liquid cultures (e.g. Czapek yeast extract broth, Mannitol Murashuge & Skoog Salts broth, and Yeast extract sucrose broth) which can be incubated for several days (e.g. 4-28 days) at about room temperature to expand the culture.

Meroterpenes can be either found to be excreted into each of the several liquid media (Czapek yeast extract broth, Mannitol Murashuge & Skoog Salts broth, and Yeast extract sucrose broth) or contained within the biomass and can be isolated from fermentation broths or biomass using liquid: liquid extraction involving EtOAc and water as well as binding the compound to a capture resin (such as HP20), washing the resin with water and then eluting the meroterpene using an appropriate solvent (such as MeOH or EtOH). Meroterpenes can be easily separated from other fungal metabolites using chromatographic techniques such as flash chromatography and a reverse-phase stationary phase (such as C-18).

The desired derivatives of spirofuranone-lactam tetramic acid can be extracted and purified from the culture liquid or the fungal biomass by any means ordinarily used for generally collecting microbial metabolites. Examples include chromatography with adsorbent such as various ion exchange resins, non-ionic adsorbing resins, gel filtration chromatography, activated charcoal, alumina and silica gel, or a separation method by using high performance liquid chromatography, or crystallisation, concentration under reduced pressure, or lyophilisation, which means can be used alone or in appropriate combination thereof, or repeatedly.

The cultures of *Peyronellaea* sp., can be obtained from natural sources or from culture collections such as Canadian Collection of Fungal Cultures (CCFC; Ottawa, Canada).

Isolates of can be cultured by methods known in the art of mycology. As a means of producing the compounds of the present invention, the producing organism can be grown on any suitable synthetic mediums or natural mediums so long as they appropriately contain carbon sources, nitrogen sources, and inorganic salts. If necessary, mediums may be suitably supplemented with vitamins and other nutrient substances.

Examples of general carbon sources include (but are not limited to), sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates. As well micro-nutrients in the form of inorganic salts can be used, for example, calcium carbonate, sodium chloride, potassium chloride, magnesium sulphate, copper sulphate, manganese chloride, zinc sulphate, cobalt chloride, and various phosphates.

The organism can be grown in an appropriate cultivation temperature within a range that allows growth of a microorganism and effective production of the compounds of the present invention. Preferred cultivation temperature is from 10° C. to 32° C., and more preferably from 20° C. to 25° C. pH at the beginning of the cultivation is preferably from about 6 to 8, and cultivation period of time is generally about one day to a few weeks.

In general, the cultivation may be terminated when a produced amount of the compound of the present invention reaches to an amount suitable for collection, preferably reaches to the maximum amount. As a cultivation method, any method can be suitably employed so far that the method is an ordinarily used, such as solid layer cultivation and normal stirring cultivation.

For example, isolates can be plated onto nutrient-containing (e.g., YM (Yeast extract Malt extract)) agar, and incubated for several days at room temperature until observable colonies appear. Individual colonies on the agar can be assayed for production of pseurotin A or comparable spirofuranone-lactam tetramic acid. Those colonies producing the desired molecules can be used to inoculate a broth culture (e.g., a YM broth culture), which can be cultured under suitable conditions (e.g., at room temperature with shaking for several days) to yield a seed inoculum. The seed inoculum can be used to initiate larger liquid cultures (e.g., Czapek yeast extract broth, Mannitol Murashuge & Skoog Salts broth, and Yeast extract sucrose broth) which can be incubated for several days (e.g., 4-28 days) at about room temperature to expand the culture.

Pseurotin A or comparable spirofuranone-lactam tetramic acid can be excreted into the broth or contained in the fungal biomass and can be isolated from fermentation broths using liquid:liquid extraction involving EtOAc and water as well as binding the compound to a capture resin (such as HP20), washing the resin with water and then eluting the target molecules using an appropriate solvent (such as MeOH or EtOH). Due to differences in polarity, pseurotin A or comparable spirofuranone-lactam tetramic acid can be easily separated from other co-produced molecules using a chromatographic technique such as flash chromatography and a reverse-phase stationary phase (such as C-18).

The anti-dandruff activity of the compounds described herein can be analysed by adapting methods well known in the art. In general, these methods involve adding the compound being evaluated for activity against *Malassezia* spp. (a fungus known to cause dandruff), and then assessing whether the compounds retard replication of the microorganism and/or directly kill the microorganism.

In particular, the anti-dandruff effect may find particular use against those *Malassezia* species associated with dandruff. This may preferably be *Malassezia furfur, Malassezia globosa*, and/or *Malassezia restricta*.

One aspect of the invention includes a method for killing or retarding the growth of a multicellular or unicellular fungus, by contacting the microorganism with the spirofuranone-lactam tetramic acid alone or the combination of biologically derivable meroterpene and the derivative of spirofuranone-lactam tetramic acid. The ability and amount of the anti-dandruff actives to kill or retard the growth of a particular microorganism can be determined by the methods described herein.

Toxicity of compositions including the anti-dandruff actives can be assessed using conventional cell- or animal-based assays. For example, as described below, keratinocyte and fibroblast cell lines can be used in an assay to determine the concentration of the anti-dandruff actives that is cytotoxic to such cells. Likewise other in vitro cellular cytotoxicity or mutagenicity assays can be used. Animal-based assays for analysing the toxicity of a compound might include acute toxicity, subchronic toxicity, chronic toxicity, carcinogenicity, reproductive toxicity, dermal toxicity, ocular toxicity, neurotoxicity, and genetic toxicity assays.

A particular feature of the active of the present invention is the combination of low cytotoxicity, good anti-dandruff activity, and stability and retention of activity even at lower pH values.

With regard to activity against anti-dandruff, the MIC of the spirofuranone-lactam used alone against *M. furfur* cells according to the method described in the examples is preferably less than 160 µg per ml, more preferably less than 140 µg per ml, further preferably less than 130 µg per ml.

With regard to activity against anti-dandruff, the MIC of the meroterpene when used in combination against *M. furfur* cells according to the method described in the examples is preferably less than 20 µg per ml, more preferably less than 8 µg per ml, further preferably less than 3 µg per ml, most preferably less than 1 µg per ml. In particular, less than 0.5 µg per ml. The MIC of the spirofuranone-lactam when used in combination against *M. furfur* cells according to the method described in the examples is preferably less than 100 µg per ml, more preferably less than 80 µg per ml, further preferably less than 60 μg per ml, most preferably less than 50 μg per ml. In particular, less than 40 μg per ml.

The amount of meroterpene and spirofuranone-lactam used to achieve the MIC when used in combination compared to the sum of the meroterpene and spirofuranone-lactam if used in individual form may preferably be less than 70% by weight. Preferably, less than 50% by weight. More preferably, less than 40%. Most preferably, less than 30%.

The fumagillin derivative described herein, and suitable salts thereof, can be included along with one or more excipients to make anti-dandruff compositions which can be administered by a variety of routes, including topical, and especially dermal.

The anti-dandruff actives can be included as active ingredients in non-pharmaceutical anti-dandruff compositions (i.e., those that usually do not require a prescription from a physician or other health care provider). Non-pharmaceutical compositions can include those that are formulated into shampoos, other hair care products (e.g. conditioners, styling products, etc.), soaps, lotions or ointments, medicated wipes, anti-fungal sprays, and the like.

The compositions can be in the form of elixirs, suspensions, emulsions, solutions, syrups, aerosols (as a solid or in a liquid medium), ointments, or lotions. Liquid forms of the compositions include aqueous solutions, aqueous or oil suspensions, and emulsions.

The anti-dandruff composition is preferably a hair care product such as a shampoo, conditioner, 2-in-1 shampoo/conditioner, hairspray, hair spritz, hair colouring product, leave-on hair tonic, hair sunscreen product, styling mousse or gel, or other hair treatment composition.

As used herein, 'effective amount' includes within its meaning a non or low toxic but sufficient amount of the anti-dandruff actives to provide the desired effect (i.e. improvement in dandruff). In particular, the amount would be sufficient to be effective to kill or retard the growth of *Malassezia furfur*, but low enough to avoid serious side effects (e.g. undue toxicity or allergic reaction).

The anti-dandruff composition according to the present invention suitably comprises in the range from 0.001 wt. % to 20 wt. %, preferably 0.01 wt. % to 10 wt. %, more preferably 0.1 wt. % to 5 wt. %, particularly 0.5 wt. % to 2 wt. %, and especially 0.8 wt. % to 1.2 wt. % of the biologically derivable meroterpene, based on the total weight of the composition.

The anti-dandruff composition according to the present invention suitably comprises in the range from 0.001 wt. % to 20 wt. %, preferably 0.01 wt. % to 10 wt. %, more preferably 0.1 wt. % to 5 wt. %, particularly 0.5 wt. % to 2 wt. %, and especially 0.8 wt. % to 1.2 wt. % of the spirofuranone-lactam tetramic acid derivative, based on the total weight of the composition.

The anti-dandruff composition according to the present invention suitably comprises in the range from 0.001 wt. % to 20 wt. %, preferably 0.01 wt. % to 10 wt. %, more preferably 0.1 wt. % to 5 wt. %, particularly 0.5 wt. % to 2 wt. %, and especially 0.8 wt. % to 1.2 wt. % of the combination of biologically derivable meroterpene and spirofuranone-lactam tetramic acid derivative, based on the total weight of the composition.

It will be understood that, when used in combination, the ratio of biologically derivable meroterpene and spirofuranone-lactam tetramic acid derivative may be adjusted as required in order to provide the desired anti-dandruff effect. In one embodiment, the ratio by weight of biologically derivable meroterpene to spirofuranone-lactam tetramic acid derivative present in the anti-dandruff composition is suitably 0.1 to 10:1, preferably 0.33 to 3:1, more preferably 0.5 to 2:1, particularly 0.8 to 1.2:1, and especially 0.9 to 1.1:1.

The anti-dandruff actives defined herein may be the only anti-dandruff actives present in the anti-dandruff composition, i.e. the anti-dandruff composition comprises only anti-dandruff actives that consist essentially of, or consist of, biologically derivable meroterpene and spirofuranone-lactam tetramic acid derivative.

In an alternative embodiment, the anti-dandruff actives may be used in combination with at least one other (i.e. chemically different) anti-dandruff active material such as anti-fungal drugs elected from any of the following: nystatin, cuprimyxin, tolnaftate, candicidin, haloprogin, iodochlorohydroxyquin, clotrimazole, undecylenic acid, proprionic acid, caprylic acid, benzoic acid, salicylic acid, griseofulvin, amphotericin B, ketoconazole, miconazole, filipin, hamycin, natamycin, rimocidin, bifonazole, butoconazole, econazole, fenticonazole, isoconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, ciclopirox olamine, flucytosine, crystal violet, piroctone olamine, zinc pyrithione, selenium sulphide, tar, and tea tree oil.

If present, preferably the other anti-dandruff actives may be selected from the group consisting of ketoconazole, zinc pyrithione (ZPT), piroctone olamine, octopirox, salicylic acid, selenium sulphide, coal tar, azelaic acid, climbazole, salicylic acid, undecylenic acid, and mixtures thereof.

One preferred other anti-dandruff active is pyrithione and/or a metal salt thereof. Any form of metal, preferably polyvalent, pyrithione salts may be used, including those in platelet and needle form. Preferred salts include those formed from the polyvalent metals magnesium, barium, bismuth, strontium, copper, zinc, cadmium, zirconium, and mixtures thereof. Zinc is preferred, particularly the zinc salt of 1-hydroxy-2-pyridinethione (known as zinc pyrithione (ZPT)).

If present, the anti-dandruff composition according to the present invention suitably comprises in the range from 0.01 wt. % to 15 wt. %, preferably 0.1 wt. % to 5 wt. %, more preferably 0.2 wt. % to 2 wt. %, particularly 0.3 wt. % to 1 wt. %, and especially 0.4 wt. % to 0.6 wt. % of at least one other anti-dandruff active (i.e. other than the anti-dandruff actives defined herein), based on the total weight of the composition.

In one embodiment, the ratio by weight of biologically derivable meroterpene and spirofuranone-lactam tetramic acid derivative to pyrithione and/or a metal salt thereof, preferably ZPT, present in the anti-dandruff composition is suitably 0.1 to 10:1, preferably 0.33 to 3:1, more preferably 0.5 to 2:1, particularly 0.8 to 1.2:1, and especially 0.9 to 1.1:1.

The anti-dandruff composition may also comprise a zinc-containing layered mineral, for example zinc carbonate (basic), hydrozincite (zinc carbonate hydroxide), aurichalcite (zinc copper carbonate hydroxide), and rosasite (copper zinc carbonate hydroxide).

If present, the anti-dandruff composition comprises in the range from 0.01 wt. % to 10 wt. %, preferably 0.2 wt. % to 5 wt. %, more preferably 0.4 wt. % to 2 wt. %, particularly 0.5 wt. % to 1 wt. %, and especially 0.6 wt. % to 0.8 wt. % of a zinc-containing layered mineral, preferably zinc carbonate, based on the total weight of the composition.

The anti-dandruff composition comprises at least one surfactant. The surfactant may be selected from anionic, non-ionic, amphoteric and/or cationic surfactants. Preferably, the surfactant may be anionic surfactant.

Suitable anionic surfactants include alkyl sulphates, alkyl ether sulphates, alpha olefin sulphonates, sulphosuccinates, isethionates, acyl amides, acyl glutamates, alkyl ether carboxylates and alkyl phosphates. The alkyl group preferably comprises in the range from 6 to 30, more preferably 8 to 20, particularly 10 to 14, and especially 12 carbon atoms. Alkyl ether sulphates and/or alkyl sulphates are preferred, particularly alkali metal, e.g. sodium, and/or ammonium salts thereof. Lauryl ether sulphate and/or lauryl sulphate are particularly preferred anionic surfactants.

In one embodiment, the anti-dandruff composition comprises both alkyl ether sulphate and alkyl sulphate, preferably lauryl ether sulphate and lauryl sulphate, suitably present at a weight ratio of 1 to 15:1, preferably 3 to 10:1, more preferably 4 to 8:1, particularly 5 to 7:1, and especially 5.5 to 6.5:1.

Surfactants can be included in an amount ranging from generally from 0.1 wt. % to 50 wt. % by weight, preferably from 5 wt. % to 30 wt. %, more preferably from 10 wt. % to 25 wt. % by weight of the total shampoo composition.

The concentration of anionic surfactant in the anti-dandruff composition is suitably in the range from 0.5 wt. % to 25 wt. %, preferably 3 wt. % to 20 wt. %, more preferably 7 wt. % to 18 wt. %, particularly 10 wt. % to 16 wt. %, and especially 12 wt. % to 14 wt. % based on the total weight of the composition.

The anti-dandruff composition may also contain at least one secondary surfactant. If present, the secondary surfactant may be selected from a non-ionic, amphoteric, betaine, and/or cationic surfactant. The total concentration of anionic surfactant and secondary surfactant(s) in the composition is suitably in the range from 3 wt. % to 50 wt. %, preferably 8 wt. % to 40 wt. %, more preferably 12 wt. % to 30 wt. %, particularly 16 wt. % to 25 wt. %, and especially 18 wt. % to 22 wt. % based on the total weight of the composition.

Suitable betaines include alkyl betaines, alkylamido betaines, alkyl sultaines, alkylamido sultaines, and mixtures thereof. Alkylamido betaines are preferred. The alkyl group preferably comprises in the range from 6 to 30, more preferably 8 to 20, and particularly 10 to 14 carbon atoms. The concentration of betaine surfactant in the anti-dandruff composition is preferably in the range from 0.1 wt. % to 20 wt. %, more preferably 0.5 wt. % to 10 wt. %, particularly 1 wt. % to 12 wt. %, and especially 1.5 wt. % to 2.5 wt. % based on the total weight of the composition.

Suitable non-ionic surfactants include the fatty alcohol acid or amide ethoxylates, alkanolamides and alkoxylated alkanolamides, monoglyceride ethoxylates, sorbitan ester ethoxylates, alkyl polyglycosides, ethylene glycol monoesters, ethylene glycol diesters, and mixtures thereof. The concentration of non-ionic surfactant in the anti-dandruff composition is preferably in the range from 0.1 wt. % to 30 wt. %, more preferably 0.5 wt. % to 10 wt. %, particularly 1 wt. % to 5 wt. %, and especially 1.5 wt. % to 2 wt. % based on the total weight of the composition.

Suitable amphoteric surfactants include alkylimino-diproprionates, alkylamphoglycinates, alkylamphoproprionates, alkylamphoacetates (mono- and di-), N-alkyl beta-aminoproprionic acids, alkylpolyamino carboxylates, phosphorylated imidazolines, and mixtures thereof. The concentration of amphoteric surfactant in the anti-dandruff composition is preferably in the range from 0.1 wt. % to 20 wt. %, more preferably 0.5 wt. % to 10 wt. %, particularly 1 wt. % to 5 wt. %, and especially 1.5 wt. % to 2 wt. % based on the total weight of the composition.

Suitable cationic surfactants include alkyl quaternaries, benzyl quaternaries, ester quaternaries, ethoxylated quaternaries, alkyl amines, and mixtures thereof. The alkyl group preferably comprises in the range from 6 to 30, more preferably 8 to 22, and particularly 10 to 20 carbon atoms.

The cationic surfactant may also be a polyquaternium material (or polyquat). Polyquats include polymers based on acrylamide and/or dimethyl allylamonium chloride such as Polyquaternium 6, Polyquaternium 7, and the like. Polymeric quaternium ammonium salts of guar gum, such as guar hydroxypropyltrimonium chloride, may be used. Polymeric quaternium ammonium salts of cellulose such as Polyquaternium 10 and the like, and polymeric quaternium ammonium salts of starch, may also be used.

If present, the concentration of cationic surfactant in the anti-dandruff composition may preferably be in the range from 0.1 wt. % to 20 wt. %, more preferably 0.1 wt. % to 10 wt. %, particularly 0.3 wt. % to 3 wt. %, and especially 0.5 wt. % to 1 wt. % by weight based on the total weight of the composition.

The anti-dandruff composition can also include other cosmetically acceptable ingredients, and in the case of hair care composition, which are suitable for topical application to the hair.

The anti-dandruff actives can be mixed with or diluted by an excipient in the anti-dandruff composition. When the excipient serves as a diluent, it can be a solid, semi-solid, or liquid material, which acts as a vehicle, carrier or medium for the active ingredient. Examples of suitable excipients include: lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

The anti-dandruff composition may additionally comprise: lubricating agents such as talc, magnesium stearate, and mineral oil; wetting agents; emulsifying and suspending agents; preserving agents such as methyl- and propylhydroxy-benzoates; sweetening agents; and flavouring agents.

The anti-dandruff composition may be formulated as transparent or opaque emulsions, lotions, creams, pastes or gels.

The anti-dandruff composition may comprise water. The amount of the water in the anti-dandruff composition may suitably in the range from 10 wt. % to 97 wt. %, preferably 30 wt. % to 95 wt. %, more preferably 50 wt. % to 90 wt. %, particularly 65 wt. % to 85 wt. %, and especially 72 wt. % to 78 wt. %, based on the total weight of the composition.

The anti-dandruff composition of the present invention may be used with one or more of the other standard ingredients or carriers used in hair care products, including shine enhancers, moisturisers, herbal additives, hair strengtheners, vitamin additives, colorants, hair thickening agents; setting and styling agents; ultraviolet absorbers; silicone oils; essential oils and fragrances; thickening or viscosity-enhancing agents; detergents; stabilising agents; emollients; chelating agents; sequestering agents; preservatives; disinfectants; anti-oxidants/radical scavengers; antistatic agents; conditioning agents; detangling ingredients; emulsifying or dispersing agents; stimulants; soothers; solvents; carriers and the like.

In particular, the anti-dandruff composition may comprise a silicone fluid or oil such as dimethylpolysiloxane, dimethyl silicone, highly polymerized methyl polysiloxane, and methyl polysiloxane, known generically as dimethicone, cyclic oligomeric dialkylsiloxanes, such as the cyclic oligomers of dimethylsiloxane, known generically as cyclomethicone. The concentration of silicone oil in the anti-dandruff composition is preferably in the range from 0.1 wt. % to 40 wt. %, more preferably 0.3 wt. % to 20 wt. %, particularly 0.5 wt. % to 5 wt. %, and especially 1 wt. % to 1.5 wt. % based on the total weight of the composition.

The anti-dandruff composition may be in the form of an aqueous "leave on" or an aqueous "rinse off" end-use product. For such compositions, a dilute solution of the anti-dandruff actives in water may be used. The concentration of the anti-dandruff actives in such a product is preferably in the range from 0.01 wt. % to 5 wt. %, more preferably 0.2 wt. % to 2 wt. %, particularly 0.5 wt. % to 1.5 wt. %, and especially 0.9 wt. % to 1.1 wt. % based on the total weight of the composition. Preferably, a buffered solution is used, in which the pH of the solution is adjusted to mildly acidic, with a pH in the range of from 4 to 6. In the case of rinse-off formulations, instructions are provided to wash off the diluted anti-dandruff actives composition after application. Depending on the level of treatment required, such instructions may also require the product to remain on the hair for some time, such as from 1 to 30 minutes. For leave-on formulations, the washing off step is omitted.

One preferred anti-dandruff product is a hair shampoo or conditioner, which functions to make the hair more shiny and manageable. The shampoo or conditioner may be in the form of a dispersion, emulsion or solution. One preferred system is one that forms liquid crystals. The liquid crystals are preferably lyotropic liquid crystals (i.e. both concentration and temperature dependent), more preferably lamellar phase liquid crystals, and particularly L alpha phase (neat) liquid crystals. The concentration of the anti-dandruff actives in the shampoo or conditioner is preferably in the range from 0.1 wt. % to 10 wt. %, more preferably 0.3 wt. % to 2 wt. %, particularly 0.4 wt. % to 1.5 wt. %, and especially 0.5% to 1 wt. % based on the total weight of the composition.

The shampoo or conditioner may contain many different types of functional ingredients such as;
  (i) cationic hair conditioning agents, e.g. ethoxylated phosphate fatty quats, such as those sold by Croda as Arlasilk™; fatty amido amines, such as those sold by Croda as Incromine™; fatty quats, such as those sold by Croda as Incroquat™ Crodazosoft™, Rejuvasoft™ or VibraRiche™ typically used at a concentration in the range from 1 wt. % to 5 wt. % based on the total weight of the composition. These are typically combined with polymeric hair conditioning cationic materials such as quaternised cellulose sold by Croda as Crodacel™, quaternised proteins, such as those sold by Croda, as Croquat™, Crolactin™, Crosilkquat™, Keramimic™ and Hydrotriticum™.
  (ii) fatty alcohols, e.g. stearyl, cetearyl, cetyl, oleyl alcohols, used typically at a concentration range of 2 wt. % to 5 wt. % based on the total weight of the composition.
  (iii) humectants or solvents, e.g. alcohols and polyols such as glycerol and polyethylene glycols, when used typically at a concentration in the range from 1 wt. % to 10 wt. % based on the total weight of the composition;
  (iv) reconstructors, e.g. hydrolysed proteins such as wheat protein, which function to penetrate the hair and strengthen the hair structure through polymer cross-linking;
  (v) glossing or detangling materials which bind to the hair and reflect light, e.g. silicones such as dimethicone, phenyltrimethicone, dimethiconol and/or trimethylsilylamodimethicone, usually at a concentration in the range from 0.2 wt. % to 10 wt. % based on the total weight of the composition;
  (vi) acidity regulators, e.g. citric acid, lactic acid, which generally maintain the pH of the conditioner at about 4 to 6;
  (vii) thermal protectors, usually heat-absorbing polymers, which shield the hair against excessive heat, e.g. caused by blow-drying or curling irons or hot rollers such as for instance those sold by Croda as Mirustyle™ MFP (quaternised starch); and
  (viii) UV protection agents, to protect hair or formulation components from degradation by UV light, such as those sold by Croda as Crodasorb™ UV-HPP.

In one embodiment, the anti-dandruff composition of the invention is in the form of an emulsion (or dispersion), such as an oil-in-water or water-in-oil emulsion, particularly an oil-in-water emulsion.

The oil phase of the emulsion will preferably be mainly an emollient oil of the type used in personal care or cosmetic products. The emollient can and usually will be an oily material which is preferably liquid at ambient temperature. Alternatively, it can be solid at ambient temperature, in which case in bulk it will usually be a waxy solid, provided it is liquid at an elevated temperature at which it can be included in and emulsified in the composition.

Suitable normally liquid emollient oils include non-polar oils, for example mineral or paraffin, especially isoparaffin, oils, such as that sold by Croda as Arlamol™ HD; or medium polarity oils, for example vegetable ester oils such as jojoba oil, vegetable glyceride oils, animal glyceride oils, such as that sold by Croda as Crodamol™ GTCC (caprylic/capric triglyceride), synthetic oils, for example synthetic ester oils, such as isopropyl palmitate and those sold by Croda as Estol™ 1512, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol™ E (propoxylated stearyl alcohol).

The concentration of the oil phase may vary widely. The amount of the oil phase in the emulsion is preferably in the range from 0.5 wt. % to 80 wt. %, more preferably 1 wt. % to 30 wt. %, particularly 1.5 wt. % to 15 wt. %, and especially 2 wt. % to 10 wt. %, based on the total weight of the emulsion.

The amount of the aqueous phase in the emulsion is preferably in the range from 20 wt. % to 99.5 wt. %, more preferably 70 wt. % to 99 wt. %, particularly 85 wt. % to 98.5 wt. %, and especially 90 wt. % to 98 wt. %, based on the total weight of the emulsion.

A wide range of emulsifiers may be employed, particularly one or more cationic emulsifier(s). The specific nature of the emulsifier surfactant used in any particular instance depends on the type of emulsion being made, particularly the amount and nature of the oil being emulsified and the total desired level of emulsifier.

The concentration of emulsifier in the emulsion is preferably in the range from 0.1 wt. % to 20 wt. %, more preferably 0.5 wt. % to 15 wt. %, particularly 1 wt. % to 10 wt. %, and especially 2 wt. % to 7 wt. %, based on the total weight of the emulsion.

The emulsion suitably comprises in the range from 0.01 wt. % to 10 wt. %, preferably 0.5 wt. % to 5 wt. %, more preferably 0.1 wt. % to 4 wt. %, particularly 0.2 wt. % to 2 wt. %, and especially 0.3 wt. % to 1 wt. % of the anti-dandruff composition based on the total weight of the emulsion.

Many other components that may be used in hair care compositions or end-use products may also be included in the anti-dandruff composition according to the present invention. These components may be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives, e.g. those sold commercially under the trade names Germaben II Nipaguard BPX and Nipaguard DMDMH, when used usually in a concentration in the range from 0.5 wt. % to 2 wt. % based on the total weight of the composition;

(ii) perfumes, when used typically at a concentration in the range from 0.1 wt. % to 10 wt. % more usually up to about 5 wt. % and particularly up to about 2 wt. %, based on the total weight of the composition;

(iii) humectants or solvents such as alcohols, polyols such as glycerol and polyethylene glycols, when used typically at a concentration in the range from 1 wt. % to 10 wt. % based on the total weight of the composition;

(iv) alpha hydroxy acids such as glycolic, citric, lactic, malic, tartaric acids and their esters; self-tanning agents such as dihydroxyacetone;

(v) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;

(vi) skin care agents such as ceramides either as natural materials or functional mimics of natural ceramides;

(vii) natural phospholipids, e.g. lecithin;

(viii) vesicle-containing formulations;

(ix) botanical extracts with beneficial skin care properties;

(x) skin whiteners such as kojic acid, arbutin and similar materials;

(xi) skin repair compounds actives such as Allantoin and similar series;

(xii) caffeine and similar compounds;

(xiii) cooling additives such as menthol or camphor;

(xiv) insect repellents such as N,N-diethyl-3-methylbenzamide (DEET) and citrus or *eucalyptus* oils;

(xv) essential oils; and (xvi) pigments, including microfine pigments, particularly oxides and silicates, e.g. iron oxide, particularly coated iron oxides, and/or titanium dioxide, and ceramic materials such as boron nitride, or other solid components, such as are used in make-up and cosmetics, to give suspoemulsions, typically used in an amount in the range from 1 wt. % to 15 wt. %, but usually at least 5 wt. % and particularly about 10 wt. % based on the total weight of the composition.

Application of the anti-dandruff composition, particularly a shampoo, to the hair typically includes working the composition through the hair. One preferred method for providing anti-dandruff efficacy comprises the steps of;

(i) wetting the hair with water;

(ii) applying an effective amount of the anti-dandruff composition to the hair; and (iii) rinsing the anti-dandruff composition from the hair using water.

These steps may be repeated, in order to obtain the desired cleansing, conditioning, and anti-dandruff effect sought.

An alternative method comprises the steps of;

(i) wetting the hair with water;

(ii) applying an effective amount of the anti-dandruff shampoo composition; (iii) rinsing the shampoo composition from the hair using water;

(iv) applying an effective amount of a conditioner composition optionally containing the anti-dandruff actives defined herein;

(v) rinsing the conditioner composition from the hair using water.

A preferred embodiment of the method is when both the shampoo composition and the conditioner composition comprise the anti-dandruff actives.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

EXAMPLE 1—FORMING & EXTRACTION OF ANTI-DANDRUFF ACTIVES

Bioassay-guided fractionation of culture extracts lead to the isolation of a biologically active metabolite produced by the fungus *Peyronellaea* sp. The isolate RKDO347 was plated out on YM (Yeast extract Malt extract) agar, and incubated for 14 d at 22° C.

Colony morphology was observed and eight explants (approximately 10 mm$^3$) were aseptically removed into 15 mL of YM broth in a sterile, capped 50 mL test tube containing 2 sterile glass coverslips and shaken at 200 rpm, 22° C. for 5 days to create a seed inoculum. A 500 µL aliquot of seed inoculum was removed into a sterile 2 mL Eppendorf tube, centrifuged at 10000 rpm for 5 min to pellet the mycelia and allow for the removal of the broth by pipetting, and stored frozen at −20° C. prior to DNA extraction. The seed inoculum was also streak plated onto YM and LB (Lysogeny Broth) agar plates, incubated for 3 days at 22° C. and inspected to ensure inoculum purity.

An additional 500 µL of seed inoculum from strain RKDO347 was dispensed into a capped 250 mL Erlenmyer flask containing autoclave sterilized Mannitol Murashuge & Skoog Salts broth medium and incubated at 22° C. for 14 days. After the incubation period, colony biomass was removed from the growth medium and the remaining broth was filtered through Whatman #3 filter paper using a glass vacuum chamber with a Buchner funnel and then partitioned into an equivalent volume of EtOAc using a seperatory funnel. The solvent extract was dried down under a stream of air prior to further chemical purification.

The EtOAc extract was re-suspended in a mixture Water:MeOH (2:8) and partitioned with hexane. The polar layer was then subjected to an automated low pressure chromatography (Combiflash) on a Diol Redisep column (30 g). The eluent system at a 20 mL/min flow rate included a 5 min isocratic step with 5% aqueous MeOH followed by a continuous gradient to 100% MeOH over 15 min and a final 100% MeOH isocratic step during 5 min. The twelve resulting fractions were analyzed by LC-HRMS and NMR and their antimicrobial and cytotoxic activities were evaluated.

Fraction 6 yielded pure pseurotin A and 10 yielded pure fumagillin derivative as identified by characteristic mass spectrometry signals (m/z corresponding to [M+H]+ and [M+Na]+ ions) and proton chemical shifts and correlations with neighbouring carbon atoms. Both compounds demonstrated anti-*Malassezia* activity.

NMR spectra were recorded on a Bruker Avance III 600 MHz NMR spectrometer and chemical shifts (δ) were referenced to the $CD_3OD$ residual peaks at $δ_H$ 3.31 ppm and $δ_C$ 49.0 ppm. Analytical mass spectrometry of all samples was carried out on a Thermo Scientific Accela UHPLC coupled with a Thermo Exactive mass spectrometer (ESI-MS) with an ESI ion source, a SEDEX 80LT ELSD, and a Thermo photodiode array (PDA) detector.

Anti-Fungal Activity Examples

The terms Minimum Inhibitory Concentration and Half Maximal Inhibitory Concentration will be understood to have the following meanings.

Minimum Inhibitory Concentration (MIC)

The minimum inhibitory concentration (MIC) will be understood to represent the lowest concentration of an anti-microbial that will inhibit the visible growth of a microorganism after overnight incubation.

Half Maximal Inhibitory Concentration ($IC_{50}$)

The half maximal inhibitory concentration ($IC_{50}$) is a measure of the effectiveness of a substance in inhibiting a specific biological or biochemical function. This quantitative measure indicates how much of a particular drug or other substance (inhibitor) is needed to inhibit a given biological process (or component of a process, i.e. an enzyme, cell, cell receptor or microorganism) by half. $IC_{50}$ represents the concentration of an active that is required for 50% inhibition in-vitro.

EXAMPLE 2—FUMAGILLIN DERIVATIVE & PSEUROTIN A ANTI-FUNGAL ACTIVITY

*Malassezia furfur* (ATCC #38593) was cultured on Media C agar for 7 d at 37° C. Yeast colonies were then harvested into 0.9% saline sterile $diH_2O$ and diluted to approximately $1.5×10^6$ CFU/mL using a 0.5 MacFarland standard (Fisher #R20410) to create an assay inoculum. Assay inoculum was added to sterile Media C broth to a final concentration of $4.5×10^4$ CFU/mL. Assays were carried out in 96 well plates with a final well volume of 100 μL.

Extract fractions and pure compounds were tested in triplicate against each organism. Extract fractions and pure compounds were resuspended in sterile 20% DMSO. Extract fractions were assayed at two concentrations (50 and 250 μg/mL) with a final well volume concentration of 2% DMSO while pure compounds were serially diluted to generate a range of eight concentrations (128 μg/mL to 1 μg/mL) in a final well volume concentration of 2% DMSO.

Each plate contained eight uninoculated positive controls (media+20% DMSO), eight untreated negative controls (Media+20% DMSO+organism), and one column containing a concentration range of a ketoconazole as a control antibiotic. The assay plate was incubated at 37° C. for 5d after which growth within the wells were visualized and photographed with a UVP Biospectrum 500 imaging system. Alamar blue was then added to each well at 10% of the culture volume (11 μL in 100 μL). Fluorescence was monitored using a BioTek Synergy HT plate reader at 530/25 excitation, 590/35 emission and 35 sensitivity at both time zero and 4 hrs after Alamar blue was added. After subtracting the time zero emission 590 nm measurement from the final reading the inferred percentage of microorganism survival relative to vehicle control wells were calculated.

At 80% confluency, the cells were counted, diluted and plated into 96 well treated cell culture plates (VWR #29442-054) at a cell density of 10000 cells per well in 90 μL of respective growth medium. All media used for the assay were the same without the addition of antibiotics. The plates were incubated at 37° C. in a humidified atmosphere of 5% $CO_2$ to allow cells to adhere to the plates for 24 hrs before treatment. DMSO was used as the vehicle at a final concentration of 1% in the wells.

All compounds to be tested were resolublised in sterile DMSO (Sigma #D2438) and a dilution series was prepared for each cell line using the respective cell culture growth medium of which 10 μL were added to the respective assay plate well yielding eight final concentrations ranging from 128 μg/mL to 1 μg/mL per well (final well volume of 100 μL) and incubated at 37° C. in a humidified atmosphere of 5% $CO_2$ for 24 hrs.

All samples were tested in triplicate. Each plate contained eight uninoculated positive controls (media+20% DMSO), eight untreated negative controls (Media+20% DMSO+cells), and one column containing a concentration range of zinc pyrithione. Alamar blue (Invitrogen #Dal1100) was added, 24 hrs after treatment, to each well at 10% of the culture volume (11 μL in 100 μL). Fluorescence was monitored using a BioTek Synergy HT plate reader at 530/25 excitation, 590/35 emission and 35 sensitivity at both time zero and 4 hrs after Alamar blue was added. After subtracting the time zero emission 590 nm measurement from the final reading the inferred percentage of microorganism survival relative to vehicle control wells were calculated.

Experimentation was carried out to assess the anti-fungal effect of the produced fumagillin derivative and the pseurotin A each on their own, and in combination against *M. furfur* in a shampoo type formulation.

Initially the *M. furfur* efficacy assay was tested with both J&J Baby Shampoo as well as Head & Shoulders to establish a baseline and assess the compatibility of the assay using a shampoo. Compositions of the fumagillin derivative with and without pseurotin A were created and suspended into the baby shampoo. The shampoo mixture was then diluted out into the assay in a similar manner to Head & Shoulders, so that various dilution points in the assay represented multiple sub-inhibitory concentrations of the fumagillin derivative and pseurotin A (concentration combinations are listed in Table 1).

The results of the anti-dandruff actives of the invention are shown in Table 1.

TABLE 1

Anti-dandruff active comparison (all values in μg/mL)

| | MIC (μg/ml) | $IC_{50}$ |
|---|---|---|
| Fumagillin derivative | 2 | 0.75 |
| Pseurotin A (sample 1) | 128 | 55 |
| Pseurotin A (sample 2) | 75 | — |
| Fumagillin derivative & Pseurotin A | 0.31 & 37.5 | — |

From this data, it can be seen that Pseurotin A alone produces an MIC response and so does the fumagillin derivative alone. A combination of 0.31 μg/ml of the fumagillin derivative and 37.5 μg/ml of pseurotin A (sub-inhibitory concentrations) produced an MIC response which suggests a synergistic effect. Each of Pseurotin A and the fumagillin derivative alone are sufficient for anti-dandruff effects, a combination of the fumagillin derivative and pseurotin A allowed for the low effective dose of the fumagillin derivative and pseurotin A to 0.31 µg/ml. These MIC values when using the actives together show a synergistic effect when compared to the MIC values of each component on their own.

This data demonstrates that when used in combination less fumagillin derivative and pseurotin A are needed in a shampoo formulation to achieve the desired effect of *M. furfur* inhibition similar to Head & Shoulders than a shampoo formulation containing either of the two active ingredients alone.

It is to be understood that the invention is not to be limited to the details of the above embodiments, which are described by way of example only. Many variations are possible.

The invention claimed is:

1. An anti-dandruff composition comprising an effective amount of:
   at least one compound selected from the group consisting of pseurotin A, pseurotin $A_1$, pseurotin $A_2$, pseurotin B, pseurotin C, pseurotin E, pseurotin D, pseurotin $F_1$, pseurotin $F_2$, asaspirenen, and synerazol; and
   at least one meroterpene represented by formula (I):

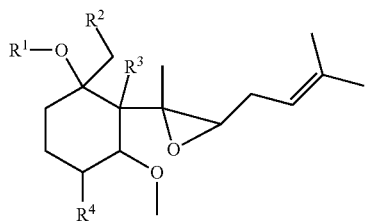

wherein:
   $R^1$ represents hydrogen and $R^2$ represents chlorine, or $R^1$ and $R^2$ together represent a single bond to form an epoxide ring;
   $R^3$ represents hydrogen or hydroxyl;
   $R^4$ represents a hydroxyl, oxygen, or —OC(O)—[CH=CH—]$_n$$R^5$ group wherein $R^5$ represents a $C_2$-$C_4$ alcohol or diol, a $C_2$-$C_4$ optionally substituted epoxide, or a carboxyl group; and
   n represents an integer in the range from 1 to 3.

2. The anti-dandruff composition according to claim 1, wherein the meroterpene comprises at least one of chlovalicin and ovalicin.

3. The anti-dandruff composition according to claim 1, wherein $R^4$ represents the —OC(O)—[CH=CH—]$_n$$R^5$ group.

4. The anti-dandruff composition according to claim 3, wherein n is 1.

5. The anti-dandruff composition according to claim 3, wherein n is 2.

6. The anti-dandruff composition according to claim 3, wherein n is 3.

7. The anti-dandruff composition according to claim 1, wherein $R^1$ represents hydrogen and $R^2$ represents chlorine.

8. The anti-dandruff composition according to claim 1, wherein $R^1$ and $R^2$ together represent a single bond to form an epoxide ring.

9. The anti-dandruff composition according to claim 1, wherein $R^4$ represents hydroxyl or oxygen.

10. The anti-dandruff composition according to claim 1, wherein the compound is at least one of pseurotin A, pseurotin $A_1$, pseurotin $A_2$ or synerazol.

11. The anti-dandruff composition according to claim 1, wherein the compound is pseurotin A.

12. The anti-dandruff composition according to claim 1, wherein the composition comprises in the range from 0.001 wt. % to 20 wt of the meroterpene, based on the total weight of the composition.

13. The anti-dandruff composition according to claim 1, wherein the composition comprises in the range from 0.001 wt. % to 20 wt of the compound, based on the total weight of the composition.

14. The anti-dandruff composition according to claim 1, further comprising at least one surfactant.

15. The anti-dandruff composition according to claim 1, further comprising at least one or more of a betaine, a non-ionic surfactant, an amphoteric surfactant, and a cationic surfactant.

16. The anti-dandruff composition according to claim 1, which is a shampoo.

17. The anti-dandruff composition according to claim 1, which is obtained from a culture of *Peyronellaea*.

* * * * *